(12) United States Patent
Campbell et al.

(10) Patent No.: US 8,287,550 B2
(45) Date of Patent: Oct. 16, 2012

(54) BONE SCREW RETAINING SYSTEM

(75) Inventors: Christopher M. Campbell, West New York, NJ (US); Todd Harrington, Golden, CO (US)

(73) Assignee: Stryker Spine (FR)

( * ) Notice: Subject to any disclaimer, the term of this patent is extended or adjusted under 35 U.S.C. 154(b) by 105 days.

(21) Appl. No.: 12/985,733

(22) Filed: Jan. 6, 2011

(65) Prior Publication Data

US 2011/0152944 A1   Jun. 23, 2011

Related U.S. Application Data

(60) Continuation of application No. 11/060,171, filed on Feb. 17, 2005, now Pat. No. 7,887,547, which is a continuation of application No. 10/331,212, filed on Dec. 30, 2002, now abandoned, which is a division of application No. 09/665,530, filed on Sep. 19, 2000, now Pat. No. 6,602,255.

(30) Foreign Application Priority Data

Jun. 26, 2000   (FR) ..................................... 00 08144

(51) Int. Cl.
*A61B 17/68* (2006.01)
(52) U.S. Cl. ........................ 606/104; 606/71; 606/286
(58) Field of Classification Search ................. 606/86 R, 606/86 A, 86 B, 280, 70, 71, 281–299, 99, 606/104
See application file for complete search history.

(56) References Cited

U.S. PATENT DOCUMENTS

| | | |
|---|---|---|
| 2,248,054 A | 7/1941 | Becker |
| 2,620,000 A | 12/1952 | Noffsinger |
| 4,857,269 A | 8/1989 | Wang et al. |
| 4,877,020 A | 10/1989 | Vich et al. |
| 4,952,236 A | 8/1990 | Wang et al. |
| 5,364,399 A | 11/1994 | Lowery et al. |
| 5,431,660 A | 7/1995 | Burke |

(Continued)

FOREIGN PATENT DOCUMENTS

DE   195 45 612 A1   6/1997

(Continued)

OTHER PUBLICATIONS

Office Action from Japanese Application No. 2001-192408, dated Dec. 10, 2010.

*Primary Examiner* — Eduardo C Robert
*Assistant Examiner* — Tara Carter
(74) *Attorney, Agent, or Firm* — Lerner, David, Littenberg, Krumholz & Mentlik, LLP

(57) ABSTRACT

An implant has a bone plate with a bone contacting surface and an opposite outwardly facing surface. The plate includes a split-ring receiving recess open to the outwardly facing surface located intermediate first and second bone screw receiving openings in the plate. The first and second bone screw receiving openings each having a slot spaced from the outwardly facing surface towards the bone contacting surface. The slot is formed in a wall of the first and second bone screw receiving openings. The slot is open to the split ring receiving recess. A resilient split-ring has a thickness less than a height of the slots in the first and second bone screw openings when measured along the bone screw receiving opening axis. The split-ring having a contracted position wherein its maximum dimension is less than a maximum dimension of the split-ring receiving recess and an expanded position wherein an outer circumference of the split-ring extends through the slots and into the first and second bone screw receiving openings.

18 Claims, 13 Drawing Sheets

U.S. PATENT DOCUMENTS

| | | | |
|---|---|---|---|
| 5,578,034 | A | 11/1996 | Estes |
| 5,797,918 | A | 8/1998 | McGuire et al. |
| 5,876,402 | A | 3/1999 | Errico et al. |
| 5,879,389 | A | 3/1999 | Koshino |
| 5,885,299 | A | 3/1999 | Winslow et al. |
| 6,090,111 | A | 7/2000 | Nichols |
| 6,102,952 | A | 8/2000 | Koshino |
| 6,139,550 | A | 10/2000 | Michelson |
| 6,152,927 | A | 11/2000 | Farris et al. |
| 6,193,721 | B1 | 2/2001 | Michelson |
| 6,258,089 | B1 | 7/2001 | Campbell et al. |
| 6,258,092 | B1 | 7/2001 | Dall |
| 6,261,291 | B1 | 7/2001 | Talaber et al. |
| 6,331,179 | B1 | 12/2001 | Freid et al. |
| 6,440,136 | B1 | 8/2002 | Gambale et al. |
| 6,458,133 | B1 | 10/2002 | Lin |
| 6,599,290 | B2 | 7/2003 | Bailey et al. |
| 6,602,255 | B1 | 8/2003 | Campbell et al. |
| 2002/0169453 | A1 | 11/2002 | Berger |
| 2004/0087951 | A1 | 5/2004 | Khalili |

FOREIGN PATENT DOCUMENTS

| | | |
|---|---|---|
| FR | 2 794 963 | 12/2000 |
| GB | 1 477 831 | 6/1977 |
| JP | 51119455 A | 10/1976 |
| JP | 63157458 A | 6/1988 |
| JP | 08275963 A | 10/1996 |
| JP | 2003504106 T | 2/2003 |
| WO | 00/78238 A1 | 12/2000 |
| WO | 01/03592 A1 | 1/2001 |

BONE SCREW RETAINING SYSTEM

CROSS-REFERENCE TO RELATED APPLICATIONS

The present application is a continuation of U.S. Ser. No. 11/060,171 filed on Feb. 17, 2005, which is a continuation of U.S. Ser. No. 10/331,212 filed on Dec. 30, 2002, now abandoned, which is a divisional of U.S. Ser. No. 09/665,530 filed on Sep. 19, 2000, now U.S. Pat. No. 6,602,255.

BACKGROUND OF THE INVENTION

The present invention relates to osteosynthesis devices for the spinal column, the devices comprising a plate and a mechanism for locking a bone screw or anchoring member in position. This divisional application relates to tools used to remove a bone screw after it has been locked in the plate.

U.S. Pat. No. 5,876,402 relates to an osteosynthesis plate comprising through-holes of conical shape capable of housing a bone screw with a completely spherical head to which is clipped, so as to form a ball-joint connection. A split coupling element of conical exterior shape complementing that of the hole is provided. A circlip reduces the aperture of the through-hole. A similar clip and groove arrangement is shown in U.S. Pat. Nos. 5,879,389 and 6,102,952.

In U.S. Pat. No. 5,876,402, the bone screw is placed in the coupling element prior to insertion in the plate. Upon insertion, the split coupling element opens up the circlip. This circlip closes up again once the coupling element has passed through. The coupling element is thus held captive in the through-hole. Final clamping of the anchoring member in position is achieved by the frictional wedging of the coupling element in the bottom of the cone.

In such a system, the number of parts makes the clamping-in position of the anchoring members weak. In addition, the clamping does not occur at the instant when the circlip closes up again after the passage of the coupling element. This leads to the risk of the assembly becoming unclamped, which is prejudicial to the patient.

FIGS. 5 and 6 of U.S. Pat. Nos. 5,879,389 and 6,102,952 show a split-ring for installation in a groove after the bone screw or anchor has been installed in the bone.

BRIEF SUMMARY OF THE INVENTION

One of the objects of the present invention is to provide a spinal implant which is easier to fit while at the same time being reliable.

With a view to achieving this objective, the present invention envisages an implant, particularly for the spinal column, comprising a joining member such as a plate exhibiting openings or orifices, bone-anchoring members such as bone screws capable of being accommodated in the orifices and at least one split ring capable of holding the members in the orifices. The split ring can come into direct contact with the anchoring member or members to hold the member or members in the orifices.

Thus, the number of parts involved in the locking is reduced and this locking can be made more reliable. Advantageously, the joining member comprises a plate and the orifices comprise an opening with a spherical seat.

Preferably, each anchoring member or bone screw comprises a complementary spherical part capable of coming into contact with the spherical seat. Thus, the surgeon has, at his disposal, freedom to orient the anchoring member angularly with respect to the joining member or plate, thus allowing him to optimize the anchorage.

Advantageously, the anchoring members or bone screws comprise driving means such as a drive socket.

In one embodiment the split ring is preferably common to at least two orifices and includes a driving means, which driving means comprise openings. In another embodiment, the split ring is specific to each orifice in the plate.

Advantageously, the split ring has a variable cross-section so as to optimize its flexibility. Thus, the ring will deform more readily when introducing the head into the orifice. The amount of time taken and the number of operations required during surgical intervention will be reduced.

The bone plate, screw and ring may be supplied as part of a screw locking system for bone plates to be used by a surgeon. The bone plate has at least one opening therein, and normally a plurality of openings, for receiving a bone screw or bone anchor. The openings extend along an axis from a top surface to a bottom bone contacting surface of the plate. Each opening has an upper region with a first diameter with a groove formed therein having a depth defined by a diameter greater than the first diameter. The plate has a lower region including a seat for the bone screw. The bone screw has a head with a maximum diameter which is smaller than the first diameter, thereby allowing the screw head to pass through that region of the opening.

An expandable ring is provided which is pre-mounted in the groove and having, when relaxed and unexpanded, an external diameter greater than the first diameter, but smaller than the groove diameter. The expandable ring has an internal diameter when relaxed and unexpanded, smaller than both the first and the head diameters. The expandable ring is capable of expanding into the groove so that the internal diameter expands to be larger than or equal to the screw head diameter while, at the same time, the external diameter is less than or equal to the groove diameter.

With this geometry, the split-ring can be pre-mounted in the groove and the screw can be inserted, shank first into the bone plate from the upper non-bone contacting surface and, upon engagement between the head of the screw and the split-ring, the split-ring expands into the groove, allowing the head to pass therethrough. Once the screw head has passed through this split-ring, it contracts under its natural spring tension. When the ring relaxes to its unexpanded state, it prevents the bone screw from backing out of the plate by the engagement of an undersurface of the split-ring and an upwardly facing surface on the bone screw.

The openings in the lower portion of the bone plate have a part spherical seat portion located between the groove and the bottom bone contacting surface of the plate with an opening in the bottom plate surface to allow the shank of the bone screw to pass through. The screw head has a corresponding part spherical surface extending from the shank of the screw towards the upwardly facing surface of the screw. Upon insertion of the screw through the plate, the screw head engages the part spherical seat on the bone plate. At that point the screw head is below the split-ring groove. The bone screw shank can be threaded in any well known fashion and may include an axial groove to enable the screw to be self-boring and self-tapping. The bone screw may include an internal bore extending along the longitudinal axis of the screw which includes threads for engaging a pull out tool should removal of the screw be necessary.

In order to enhance the locking system's ability to prevent the screw from backing out of the bone plate, both the groove and split-ring have complementary inclined surfaces extending towards the upper surface of the bone plate upon moving towards the center of the opening in the radial direction. The engagement of the surfaces in combination with a force exerted by the screw on the bottom surface of the split-ring causes the internal diameter of the ring to decrease with increasing force from below. This insures the bone screw cannot back out of the opening.

In order to make the insertion of the bone screw easier, it is provided with an inclined surface complementary to an inclined surface on the internal bore of the split-ring, which inclined surfaces increase in diameter upon moving in a direction from the bottom surface of the plate towards the upper surface of the plate and radially outwardly of the opening central axis. Thus, when the screw head inclined surface engages the complementary inclined surface on the internal diameter of the split-ring, forces are generated which expand the split-ring into the groove. In order to increase the flexibility of the split-ring, at least one cutout and preferably three or more cutouts are spaced around the external diameter of the ring, resulting in a variable cross-section. This allows the ring to have more flexibility in expanding than if the external diameter of the ring were constant. In order to better prevent the egress of the bone screw from the plate, the surface of the split-ring facing towards the bottom of the plate is flat and extends generally perpendicularly to the central axis through each opening. The bone screw has a complimentary upwardly facing generally flat or slightly inclined surface.

The location of the groove in the plate is such that when the head of the screw fully engages the spherical seat in the plate, the upwardly facing surface is located below the bottom surface of the split-ring. In order to allow the bone screw to rotate from side to side once seated, an angular cutout of 0° to 20° can be provided at the bottom surface of the plate, thereby making the opening on the bottom surface oblong in at least one direction. This allows the longitudinal axis of the screw head and shank to be rotated between 0° and 20° with respect to the central axis of the opening.

The material for the split-ring must be flexible and be compatible with the body and it has been found that the titanium alloy disclosed in U.S. Pat. Nos. 4,857,269 and 4,952,236, which have modulus of elasticity not exceeding 100 GPa, is acceptable. Polymeric materials such as ultra-high molecular weight polyethylene are also acceptable.

The joining member or plate may be curved to match the anatomical curvatures. Thus, the implant curved to best suit the anatomy and natural curvature of the spinal column in the case of a spinal application. Of course, the plate may be used in fracture fixation, as a tibial baseplate, as a hip side plate or any application where bone plates and screws are used. For these uses, a larger screw than that described herein is necessary. The screw locking system can be scaled up from that described herein so that any size screw can be utilized in a smaller locking system.

Also envisaged is a method for implanting the implant involving accessing the spinal column via an anterior route, fitting the implant, preparing the anchorage, fitting the anchorage members, locking the implant and the head of the anchoring members with respect to the joining member, and closing up the access route.

These and other objects and advantages of the present invention will become apparent from the following description of the accompanying drawings. It is to be understood that the drawings are to be used for the purposes of illustration only and not as a definition of the invention.

BRIEF DESCRIPTION OF THE DRAWINGS

Other features and advantages of the invention will become more apparent on reading the description which follows of the preferred embodiments which are given by way of non-limiting examples.

FIG. 4b is an elevation view of the first embodiment shown in FIG. 4a;

FIG. 4c is a front view of the first embodiment shown in FIG. 4a;

FIG. 8b is an elevation view of the second embodiment shown in FIG. 8a;

FIG. 8c is a front view of the second embodiment shown in FIG. 8a;

DETAILED DESCRIPTION

Figure 1:
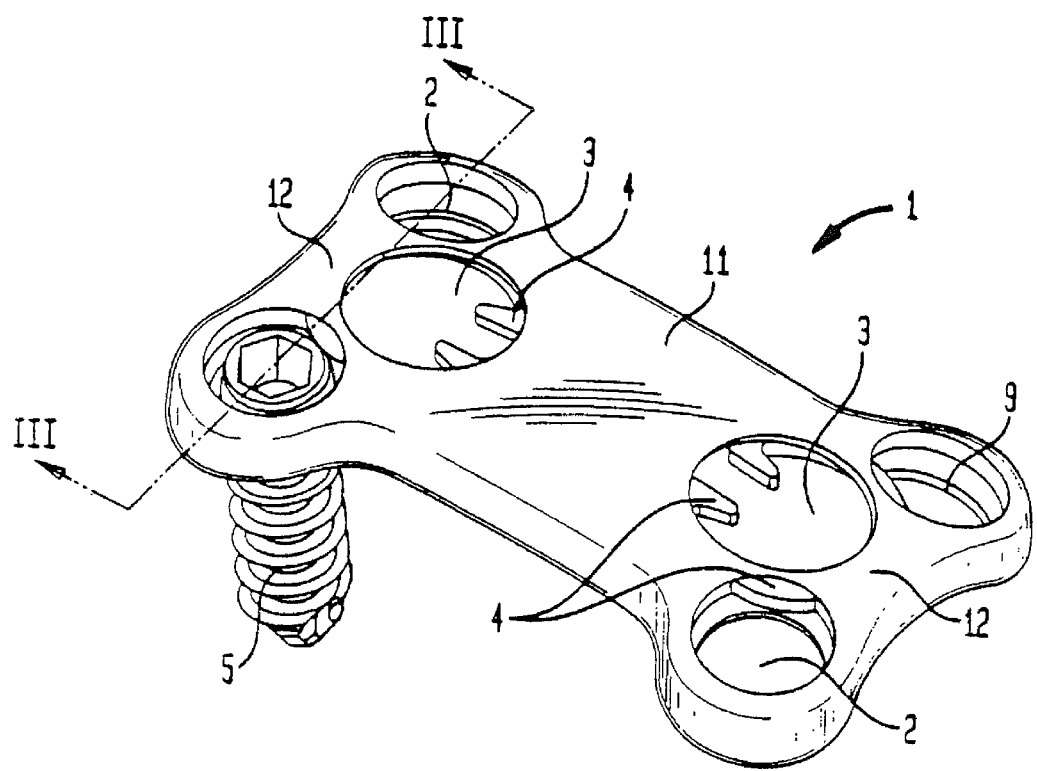
FIG. 1 is a perspective view of a first embodiment of the invention.
Figure 2:
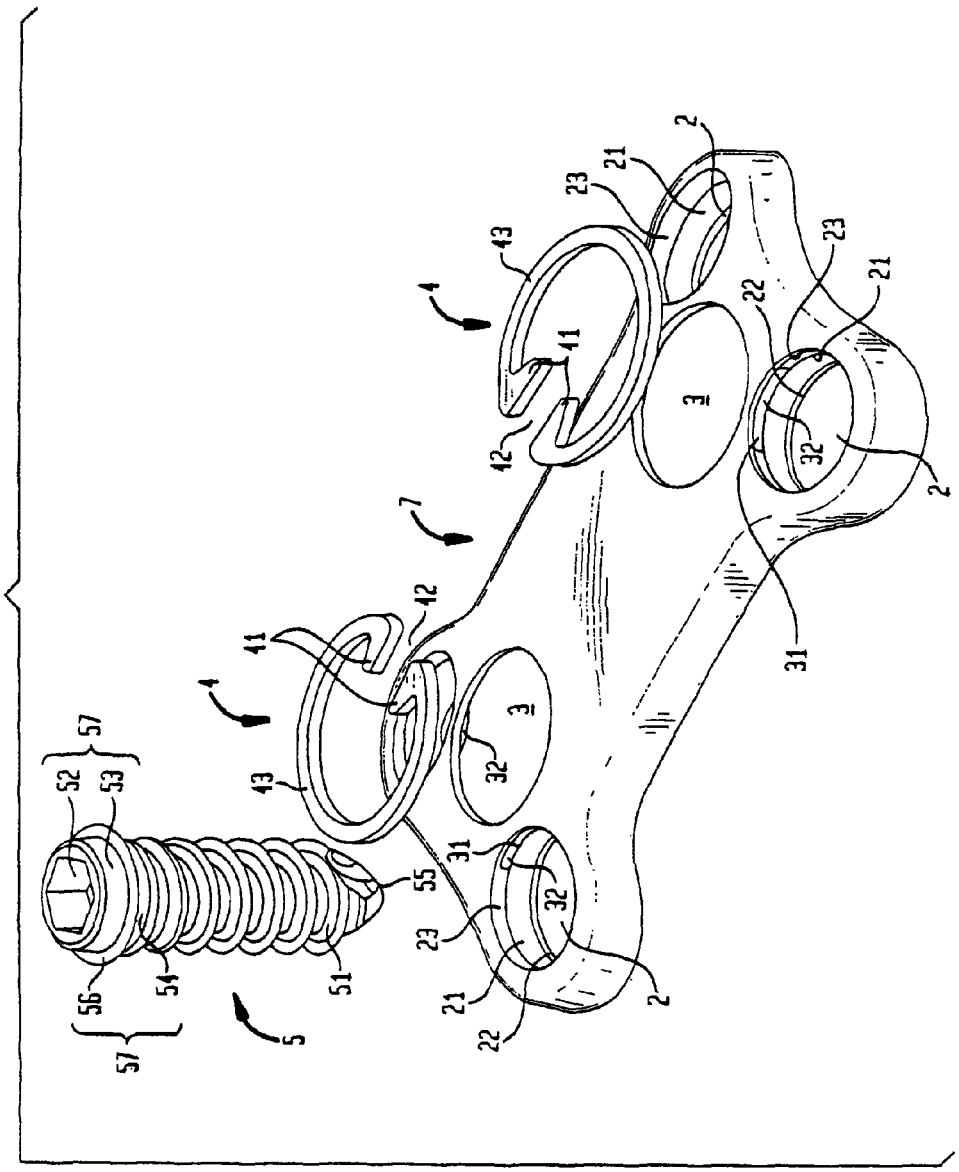
FIG. 2 is an exploded perspective view of the first embodiment.
Figure 3:
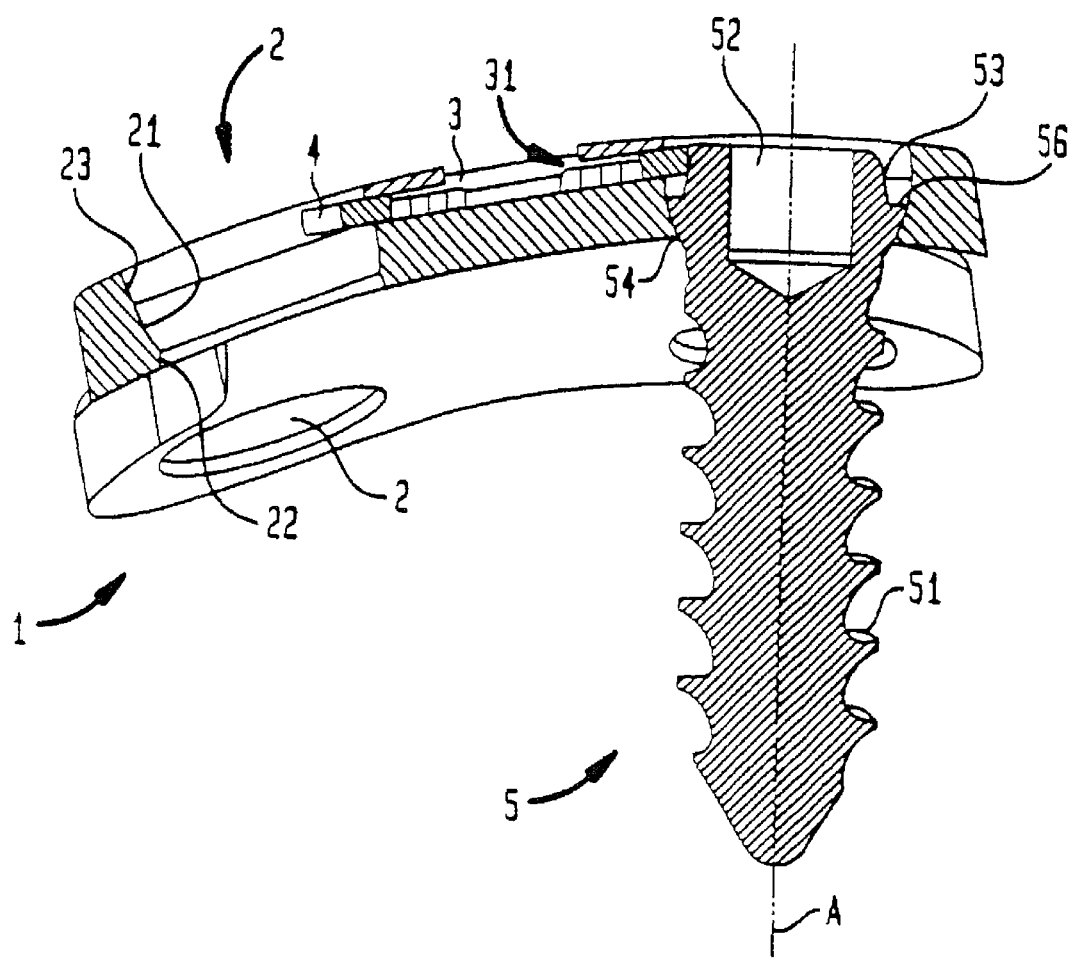
FIG. 3 is a cross-sectional view along lines III-III of the first embodiment of FIG. 1.

With reference to FIGS. 1 to 4c, there is shown the implant according to the first embodiment comprises a plate 1, bone screws 5 and circlips or split-rings 4. The plate 1 is a bone plate such as an anterior cervical plate or any other plate designed to be held on bone by bone screws. Plate 1 may join two bone parts or stabilize a fracture or may sit on a resected bone surface such as on a tibial plateau.

In the preferred embodiment, plate 1 is formed of a body 11 ending in two ends 12 which have a width slightly greater than that of a mid-zone of body 11. Each of the ends comprises a pair of openings or orifices 2 which pass through the entire thickness of plate 1. The four openings are arranged geometrically as at four corners of a rectangle. Each of the openings 2 has a first, upper, cylindrical part 23 which continues in the form of a spherical central part 21 and ends in a second, lower, cylindrical part 22, the diameter of which is smaller than that of the first cylindrical part 23. The spherical intermediate part 21 allows the angle of the bone screw 5 that is to be accommodated in the opening 2 to be chosen.

Plate 1 preferably comprises two blind holes 3 which have a circular opening and a recess 31. The two blind holes are arranged on the longitudinal mid-segment of the rectangle, near the respective pairs of corners. Recess 31 is such that it protrudes into the pair of openings 2 to which it is adjacent, thus creating an open slot 32 in each opening 2 of the pair. This slot 32 is made in such a way that it is located in the first cylindrical part 23 of the openings 2.

Figure 4A:
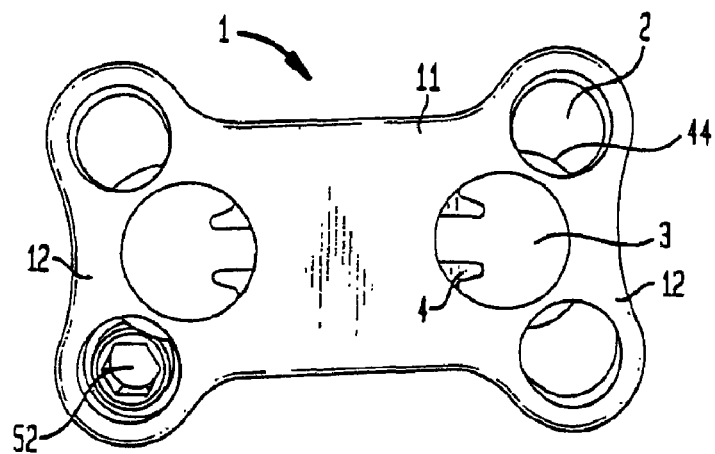
FIG. 4a is a plan view from above of the first embodiment.
Figure 4B:
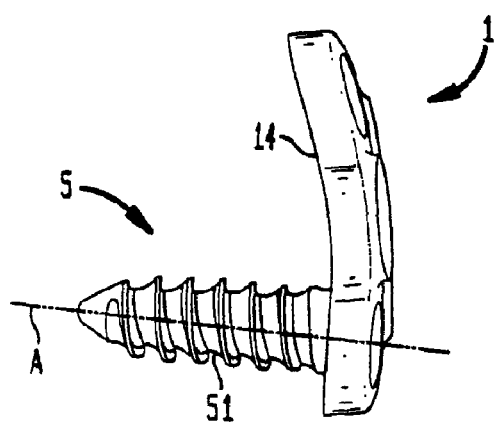
Figure 4C:
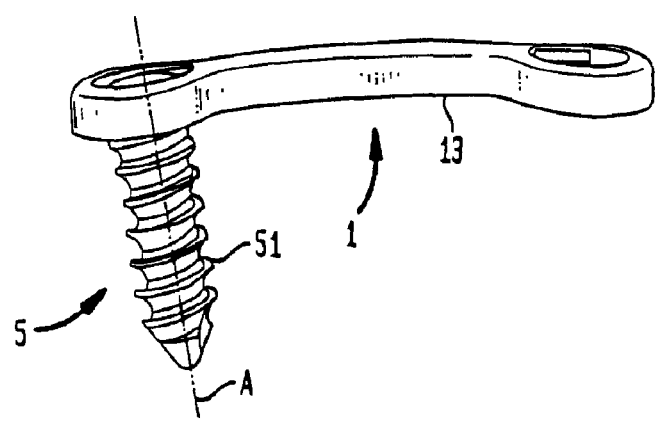
Figure 5:
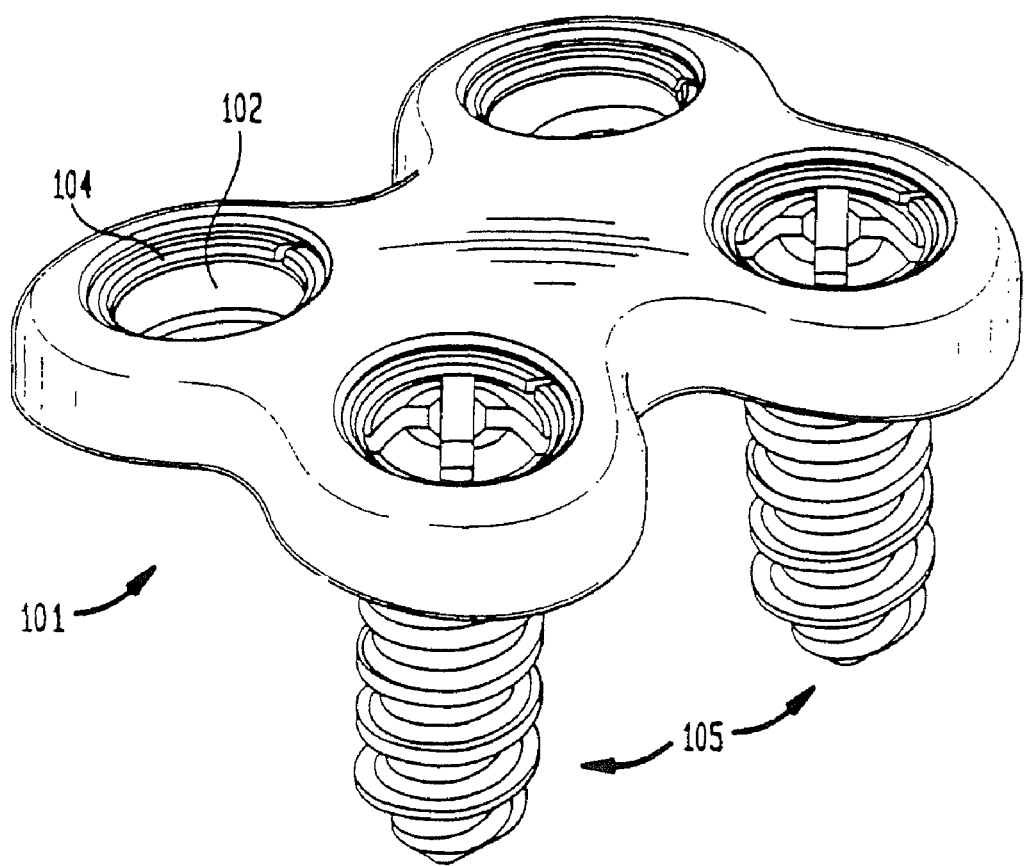
FIG. 5 is a perspective view of a second embodiment of the invention.
Figure 6:
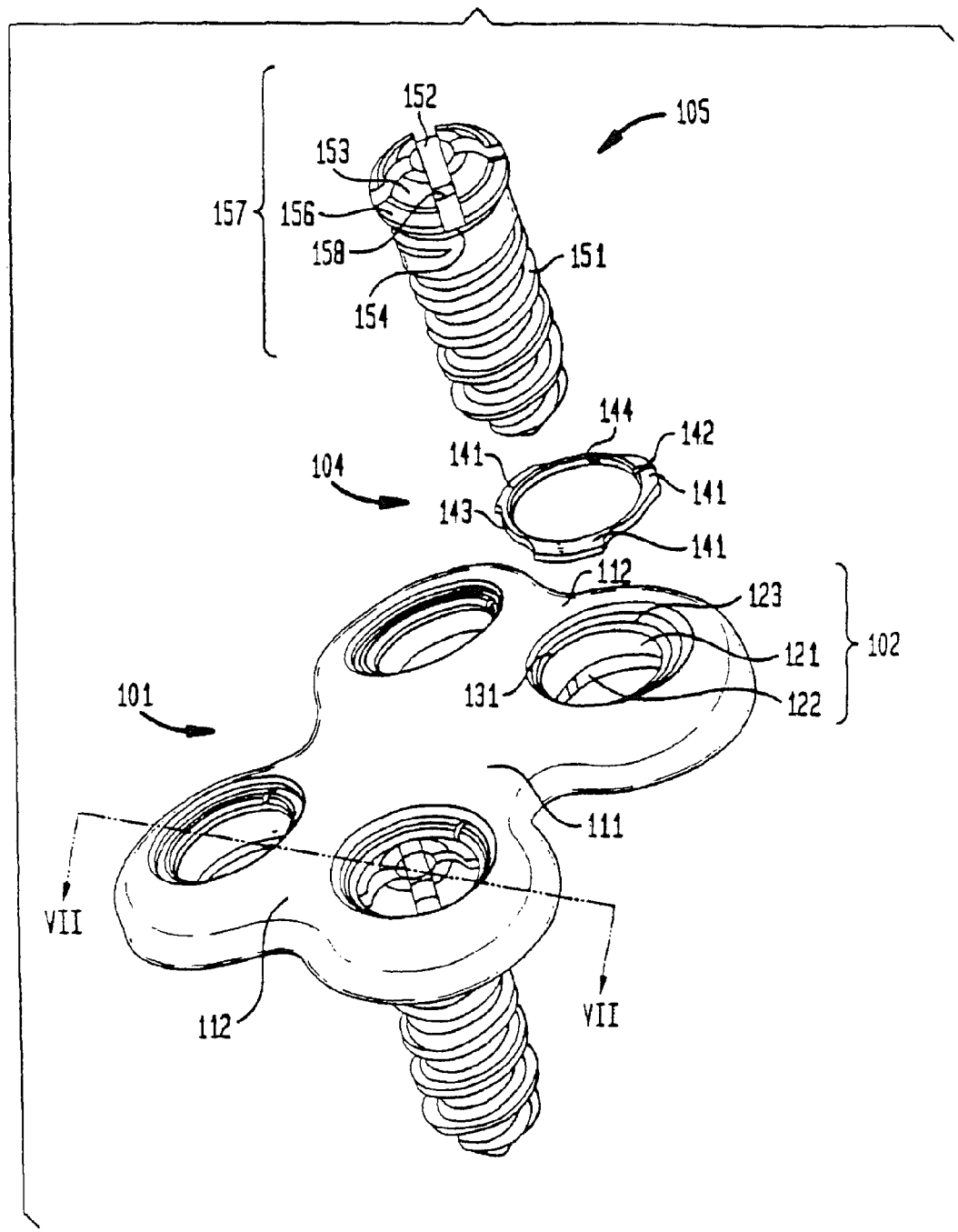
FIG. 6 is an exploded perspective view of the second embodiment.

Plate 1 has a first curvature 13 in its longitudinal plane, as depicted in FIG. 4c. This curvature 13 allows plate 1 to follow the natural lordosis of the section of spine for which the plate 1 depicted in FIGS. 1 to 4c, is intended. In addition, the plate 1 has a second curvature 14 in its transverse plane as depicted in FIG. 4b. This curvature 14 allows plate 1 to match as closely as possible the shape of the body of the vertebra to which it is connected.

Each recess 31 is capable of housing a circlip 4. The circlip 4 is in the form of a circular ring 43 split at 42. The circlip or split-ring 4 comprises driving means 41 which, in this embodiment, are lugs projecting towards the inside of the ring. Each lug may be shaped to receive the tips of a pair of needle nose pliers (See FIG. 9).

Once in place in the recess 31, with the circlip 4 in the position of rest, i.e. in the open position, it protrudes into the pair of openings 2 adjacent to it through the slot 32 of each opening 2. It thus closes up the opening 2 slightly.

The bone screw 5 is the preferred anchoring member in the embodiment which allows the plate 1 to be connected to the bodies of the vertebrae which are fitted with the present invention. The preferred screw 5 has a head 57 surmounting a cylindrical part or shank with a thread 51 suited for bone, comprising a self-tapping means 55 at its distal end. These tapping means allow the screw to better penetrate the bone when being driven. The head 57 comprises a drive 52 which, in this instance, is embodied by a hexagonal socket. In addition, the head 57 comprises a slightly conical part 53 which is continued in the form of a part 56 forming a rim extending towards the outside of the screw 5 and inclined slightly with respect to a plane perpendicular to the axis A of the screw 5.

Finally, the head 57 of the screw 5 ends in a spherical male part 54 which complements the female intermediate part 21 of the opening 2 and which meets the threaded cylindrical part or shank 51. These complementing forms allow the bone screw 5 to be set at a chosen angle with respect to plate 1. The anchoring of plate 1 can thus be optimized by the surgeon during the operation.

Preferably, the implant of the present invention shown in FIGS. 1-4 is supplied to the surgeon with the two circlips 4 installed in recesses 31 of plate 1. If the plate is an anterior cervical plate, it is preferably implanted by an anterior access route and by uncovering the vertebral bodies that will be fitted. The surgeon positions the plate 1 then pierces pilot holes through each pair of openings where he wishes to have an anchorage. He then engages a bone screw in each pilot hole. He screws these in until the part 54 of their head 5 comes into contact with the part of the ring 44 of the circlip 4 that projects through the orifice 32. At this point, there are two possible options:

1. The surgeon closes up the circlip 4 by bringing the two lugs 41 closer together using pliers and then, holding the circlip closed, he screws the two bone screws 5 in until the complementary spherical parts 21 and 54 come into contact, then, releasing the circlip which returns to the open position over the rim 56;

2. The surgeon continues to screw in the anchoring member 5, the spherical part 54 pushing the ring 44 into the slot 32 through a ramp effect and thus forming its passage, and the ring will open again automatically once the rim 56 has passed by, and the complementary spherical parts 21 and 54 will be in contact.

Locking is provided by contact between the complementary spherical parts 21 and 54 and by the re-opening of the circlip 4 above the rim 56. The second role of the rim 56 is to limit the possibilities of angular orientation. This prevents the screw from coming out of the vertebral body or from coming into contact with its counterpart fitted in the other opening 2 forming the pair. In both instances, the plate would be poorly anchored or even not anchored to the vertebral body at all. Thus, having introduced each screw into the orifice via its distal end, the circlip prevents the screw from backing out of the orifice.

In the event of an adjustment, the surgeon can easily withdraw the plate 1 simply by unscrewing the bone screws 5 after having closed up the circlips 4 by moving their lugs 41 closer together, thus uncovering the aperture of the orifice 2.

In a second embodiment illustrated by FIGS. 5 to 8c, cervical plate 1 is preferably still formed of a body 111 ending at two ends 112 which are slightly wider than the body 111. Each of the ends 112 still has a pair of openings 102 which pass right through the entire thickness of the plate 101. Each opening 102 has a first part 123 which is cylindrical, then a spherical intermediate part 121. Preferably, the orifice or opening 102 has a part 122 in the form of an angular cutout in the lengthwise direction of the plate 101. Preferably, the cutout allows the screw to pivot an angle B, preferably from 0° to 20°, in the lengthwise direction about axis 164, preferably the width of the cutout 122 is slightly less than its length. A circular recess or groove 131 is formed in the cylindrical part 123 of each opening 102. As in the previous embodiment, when used as an anterior cervical plate, the plate 101 has a curvature 13 in its longitudinal plane and a curvature 14 in its transverse plane. The roles of these curvatures are the same as in the previous embodiment.

The recess 131 is able to accommodate a circlip or split-ring 104. As before, the circlip 104 is in the form of a circular ring 143, split at 142. The preferred circlip or split-ring 104 in this instance has tabs 141 and cutouts 149 distributed uniformly around the entire circumference of the ring 143. Preferably, there are at least 3 of these tabs. They make it possible to be sure that the circlip will not escape from the groove or recess 131, while leaving thinner parts of the ring 143 to allow better flexibility when deforming or expanding the circlip as will be discussed hereinbelow. Of course it is possible to make the ring thinner or use other means to achieve flexibility in the ring. For example, one or two tabs could be used if the cutouts in the ring are sized sufficiently to produce the required flexibility. The circlip 104 comprises expansion chamfer or ramp 144 in the form of an inlet chamfer located on the interior side 145 of the ring 143.

The bone screw 105 differs from that of the previous embodiment in that the drive 152 which is in the form of a cross is extended in one embodiment by a blind bore 158 coaxial with the axis A of the screw 105. This allows the use of a screwdriver with a flat or cruciform blade extended by a small cylindrical protrusion that complements the blind bore 158. Thus, when tightening or loosening, the screwdriver cannot slip to injure nearby living tissues or irreversibly deform the circlip 104, as this would compromise locking.

The preferred head 157 has a part 153 which is generally conical and which slightly bows outwardly which is continued radially outward by a part 156 forming an upwardly facing rim surface extending towards the outside of the screw 105 and which preferably is slightly inclined with respect to a plane perpendicular to the axis A of the screw 105.

Finally, a part spherical portion 154 that complements the intermediate part 121 of the opening 102 allows the outer edge of the portion 154 to meet the threaded cylindrical part or shank 151, which is threaded with a bone-screw thread. The purpose of this complementing nature is to allow the angle of the screw 105 to be chosen with respect to the plate 101 in order to optimize anchorage.

As in the previous embodiment, the implant is supplied to the surgeon with the four split-rings or circlips 104 installed in the four recesses 131 in the plate 101. As before, the surgeon, having made his access route, then positions the plate 101 and pierces the pilot holes through the pairs of openings 102 where he wishes to anchor, completely screws in the bone screws 105. At the end of tightening, the spherical part 154 will come into contact with the chamfer 144 of the circlip 104 and then, through a bearing action, open up the latter to make its passage towards the spherical intermediate part 121 of the orifice 102. The circlip 104 will close back up again automatically once the rim 156 has passed, and the complementary spherical parts 121 and 154 will be in contact.

Performing these two operations makes sure that the screw 105 is locked in the plate 101. As before, the second role of the upwardly facing rim 156 is to limit the possibilities of angular adjustment. This prevents the screw from coming out of the vertebral body or its threaded shank 151 from coming into contact with its counterpart fitted in the other orifice 102 forming the pair. In both instances the plate would be poorly anchored or not anchored to the vertebral body at all. In the event of an adjustment, the surgeon can easily withdraw the plate 101 simply by unscrewing the bone screws 105 after having opened up circlip 104 as will be discussed below.

Figure 7:
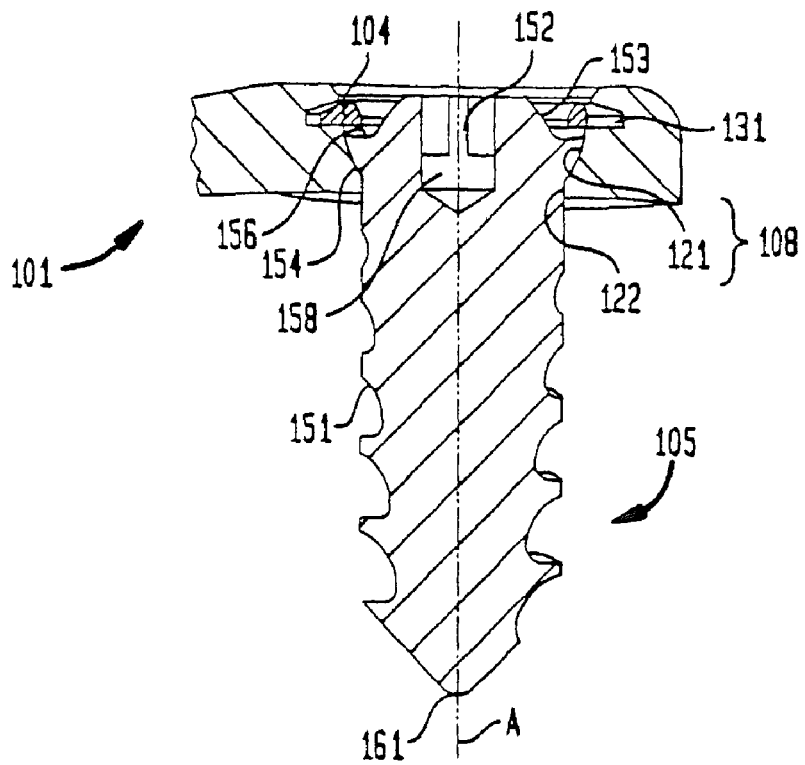
FIG. 7 is a partial view in section on the plane VII-VII of the second embodiment.
Figure 7A:
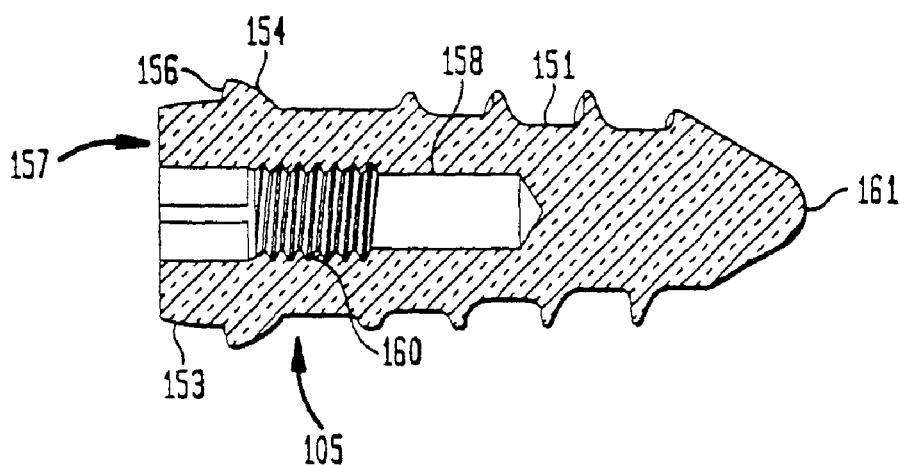
FIG. 7a is a cross-sectional view of a bone screw or anchor of the present invention.

A preferred bone screw of the second embodiment of the present invention is shown in greater detail in FIG. 7a. In the preferred embodiment, the blind bore 158 of screw 105 is threaded for a portion 160 located below drive 152 towards the tip 161 of the screw. The function of the threaded portion will be described in greater detail below.

It should be noted that the preferred screw 105 has a nominal thread diameter of about 4 mm with the outer diameter of the upwardly facing surface rim 156 being about 5 mm. If desired, the leading end or tip 161 of the screw shank 151 may include a groove or other structure for allowing the bone screw to be self-drilling and self-tapping. In this situation, no pilot hole need be drilled by the surgeon.

Figure 7B:
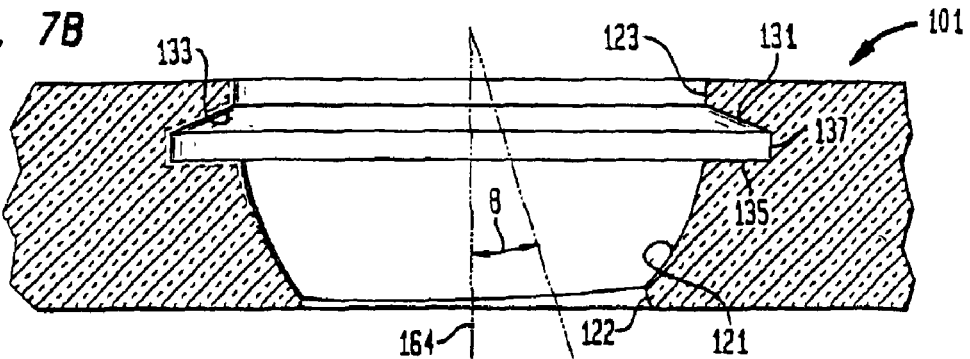
FIG. 7b is a cross-sectional view of a single orifice used in the second embodiment of the invention without the screw and split-ring along line VII-VII of FIG. 6.

Referring to FIG. 7b, there is shown the preferred opening 102 in the bone plate. The recess or groove 131 which accommodates spring clip 104 has an upwardly and inwardly inclined surface 133 which, in the preferred embodiment, extends at an angle of about 20° with respect to the bottom surface 135 of groove 131. In the preferred embodiment, the bottom surface 135 of groove 131 extends along a plane perpendicular to the axis 164 of the opening 102. The upper inclined surface 133 is spaced from surface 135 by surface 137 which, in the preferred embodiment, is about 0.3 mm. The maximum diameter to surface 137 of groove 131 is, in the preferred embodiment, about 6.9 mm. Spherical seat 121 for screw head 157 extends from adjacent the bottom bone contacting surface of the plate to surface 135. In the preferred embodiment, the spherical surface has a radius of 2.67 mm.

Consequently, the part spherical portion 154 of the screw has a similar radius. As can be seen in FIG. 7b, the opening 102 may have an angular cutout along a portion of surface 122 adjacent the bottom plate surface to allow the shank 151 of the screw to extend in at least one direction at an angle B of approximately 0° to 20° and preferably 10° with respect to the axis 164. Thus, when viewed from the bottom, the opening would appear to be oblong in at least one direction. Of course, the angular cutout can be enlarged to permit angulation in a plurality of directions.

Figure 7C:
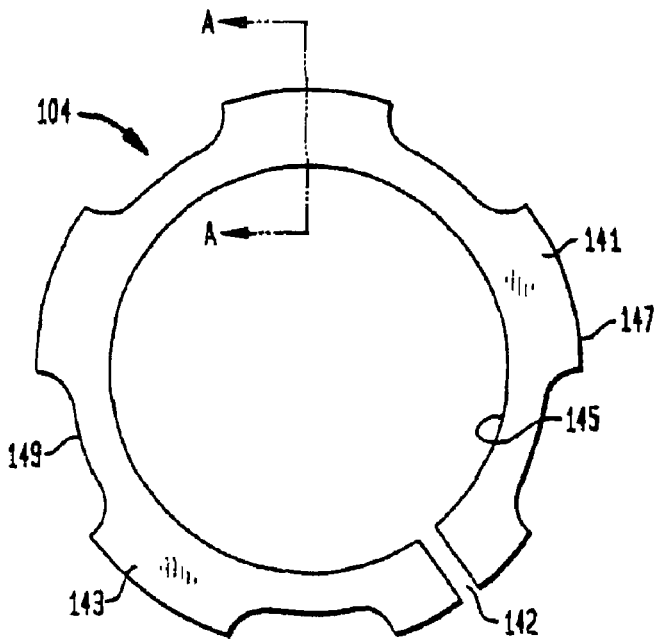
FIG. 7c is a plan view of the split-ring of the second embodiment of the present invention.

Referring to FIG. 7c, there is shown a preferred split-ring or circlip 104 which includes five tabs 141 distributed uniformly around the circumference of the ring 143. In the preferred embodiment, the ring has an internal diameter 145 of approximately 4.5 mm and a maximum external diameter 147 of preferably 6.2 mm. The difference between the external diameter 147 and the groove diameter 137 is preferably about 0.7 mm. This allows the internal diameter to expand to accommodate the screw head. The preferred cutouts have a depth of approximately 0.4 mm so that the external diameter 149 at each cutout is approximately 5.4 mm. The preferred split 142 is 0.26 mm in width when the split-ring is in its relaxed, i.e. unexpanded condition. The above dimensions are given for illustration only and larger screws, openings and split-rings may be used in other applications.

Figure 7D:
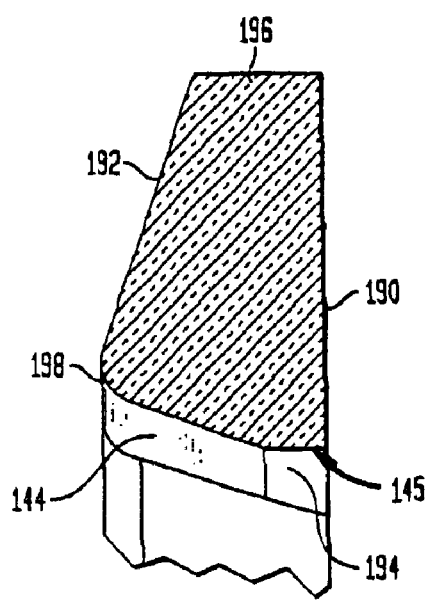
FIG. 7d is a cross-sectional view of the split-ring of FIG. 7c along lines A-A.
Figure 8A:
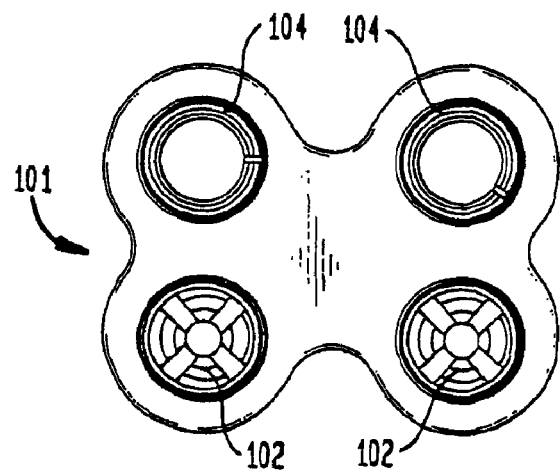
FIG. 8a is a plan view of the second embodiment of the invention.
Figure 8B:
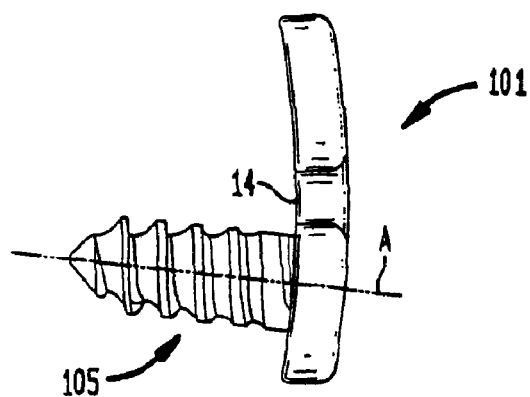
Figure 8C:
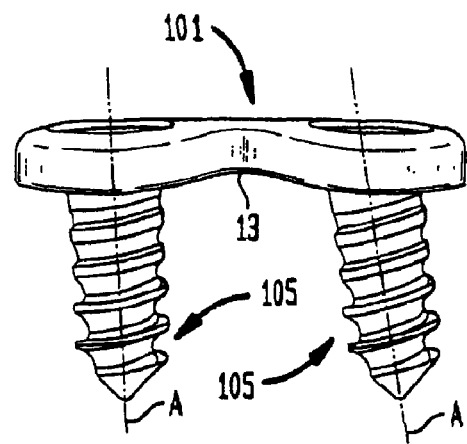

Referring to FIG. 7d, there is shown a cross-section of the split-ring shown in FIG. 7c along lines A-A. The split-ring has a bottom surface 190 oriented to engage the bottom surface 135 of groove 131. The cross-section has an inclined upper surface 192 for engaging surface 133 which is upwardly inclined on moving towards the center the split-ring. Preferably, the incline is at an angle of about 20° with respect to bottom surface 190. The surface forming internal diameter 145 is in two sections, the first is surface 194 which is generally parallel to axis 164 of opening 102 and the second is surface 144 which is angled radially outwardly towards surface 192 also at preferably 20° with respect to surface 194 (and the axis 164). Surfaces 192 and 144 are preferably connected by a radius 198 rather than a sharp corner. The preferred split-ring has an overall height from the surface 190 to the top of radius 198 of approximately 0.52 mm and the distance along surface 196 between surface 190 and 192 is about 0.29 mm.

The preferred cross-section allows spring-clip 104 to be assembled within groove 131 by the plate manufacturer and shipped to the user in a pre-assembled condition. It is especially important that the clip 104 have a sufficient number of cutout areas to render it sufficiently flexible for insertion into the inserting recess or groove 131 prior to shipping to the end user. It is also necessary to use a relatively flexible material for the ring, which material has a modulus less than 100 GPa. Such a titanium material is found in U.S. Pat. Nos. 4,857,269 and 4,952,236. If these titanium alloys are utilized for the split-ring, it has been found that advantageous to make the joining member or plate and anchoring or bone screw out of the same material, although such is not absolutely necessary. In addition, polymeric materials can be used for the split-ring. In the preferred embodiment, the split ring 104 has no means for enabling its removal from the groove after assembly. Thus, it is not possible for the surgeon to remove the ring from the plate.

Another advantageous feature of the split-ring is the preferably 20° incline of the top surface 192 which engages with complementary groove surface 133. This is advantageous because forces generated from the backing out of the screw 105 against the bottom surface 190 of split-ring 104 tend to keep the inner diameter 145 from expanding. In addition, only a small annular inter-engagement between the bottom surface 190 of ring 104 and the upwardly facing surface 156 is necessary to prevent screw 105 from backing out of hole in plate 1. In the preferred embodiment, this annular overlap is at least 0.07 mm and preferably between 0.07 mm on a radius and 0.11 mm.

Figure 9:
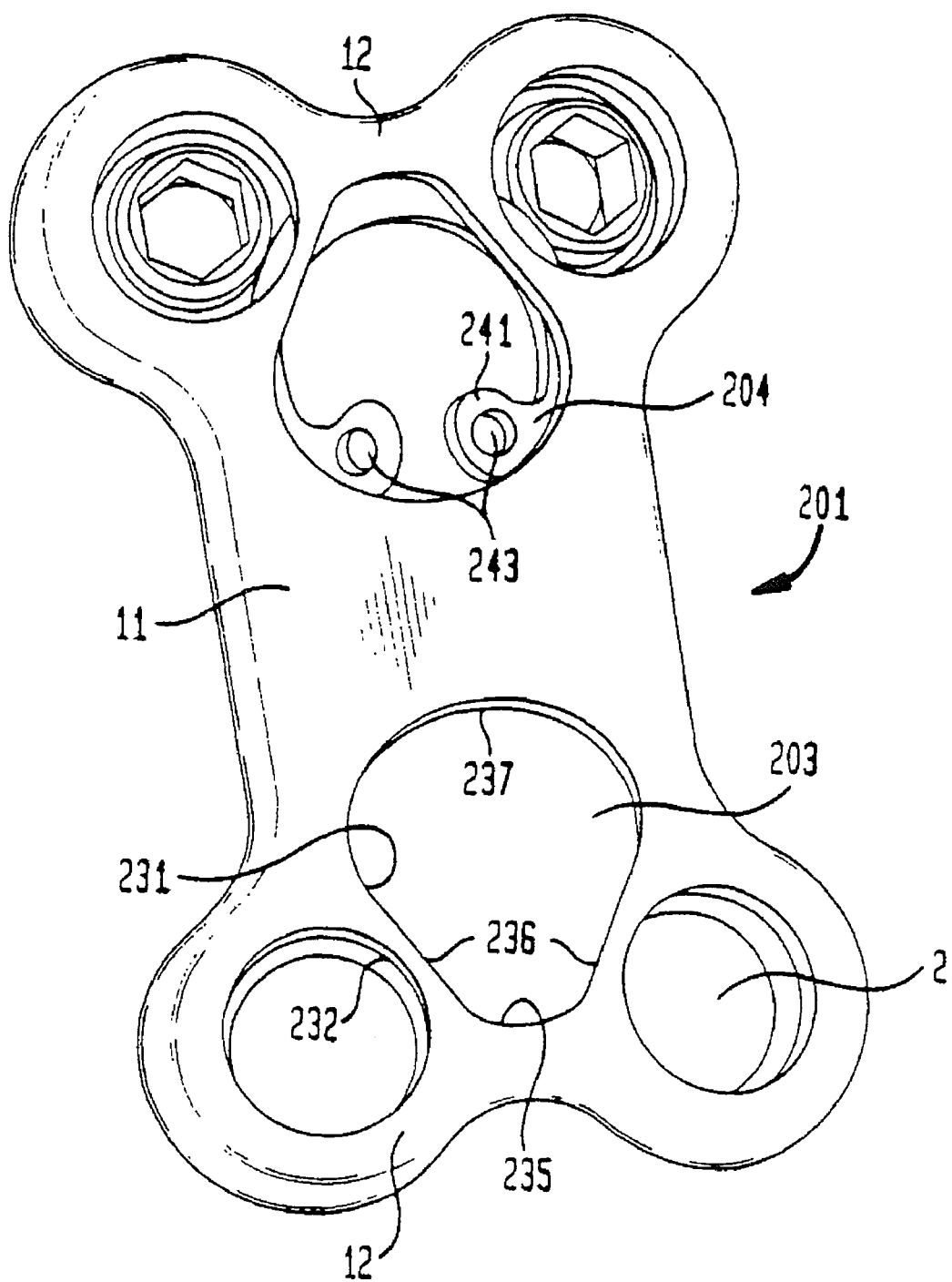
FIG. 9 is a perspective view of a third embodiment of the invention.

In a third embodiment illustrated in FIG. 9, the device 201 differs from a first embodiment only in the shape of the blind holes 203 and of the circlip 204 that can be housed in the recess 231. The shape of the holes 203 has a semicircular base 237 continued by two straight surfaces 236 which converge towards each other and are connected at their other end of the side of the associated orifices 2 by a semicircular vertex 235 of smaller radius than the base 237. This shape facilities the fitting of the circlip 204. The latter is very similar to the one in the first embodiment, except for the lugs 241 which have holes 243 to take the jaws of a driving instrument. Installation with this embodiment is identical to that of the first embodiment.

The circlip 104 may have a constant cross-section.

The bone screws may be monoaxial: they cannot be oriented with respect to the plate.

It can thus be seen that, in the embodiments of FIGS. 1 and 9, one and the same circlip locks two anchoring screws.

In all these embodiments, each circlip collaborates by direct contact with the screw to prevent it from coming out of the opening, without it being necessary to provide a part acting as an intermediate between the circlip and the screw.

Figure 10:
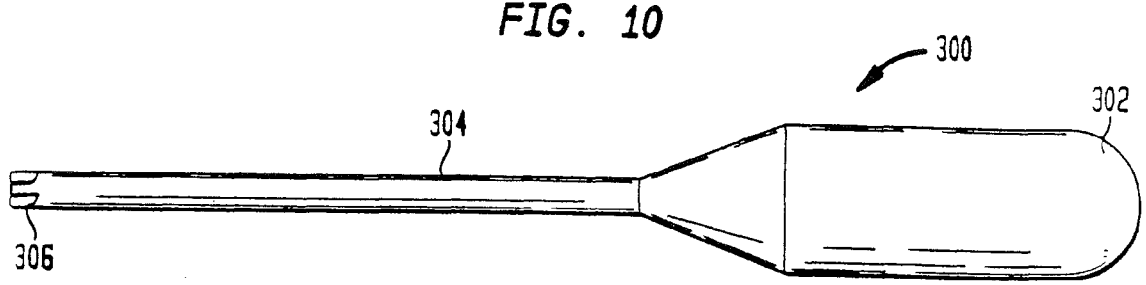
FIG. 10 is a plan view of a screw driver for driving the bone screws of FIG. 7a from the orifice of FIG. 7b.
Figure 10A:
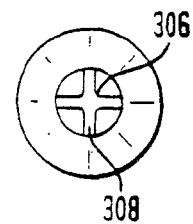
FIG. 10a is an end view of the screw driver shown in FIG. 10.

Referring to FIG. 10, there is shown a plan view of the preferred screwdriver 300 for driving screw 105. The screwdriver 300 includes a handle 302, a shaft 304 and a drive head 306. Referring to FIG. 10a, there is shown an end view of drive head 306 showing a cruciform drive having a pair of mutually perpendicular blades 308. Blades 308 engage drive 152 on screw 105. In the preferred embodiment, the depth of the cruciform slot forming drive 152 is about 2 mm and the depth of the drive blades 308 is somewhat less and the width of the four slots forming drive 152 are about 1 mm with the width of the blades 308 being slightly less. This geometry ensures excellent engagement between the blades on the driver 300 and the drive 152.

Figure 11:
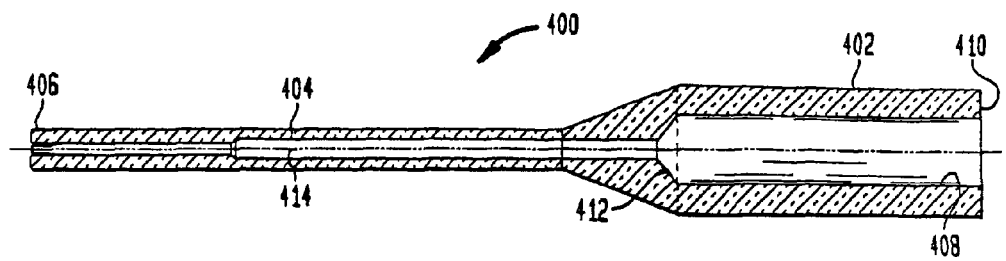
FIG. 11 is a plan view of an extractor tube for extracting the anchor or bone screw from the plate after implantation.
Figure 11A:
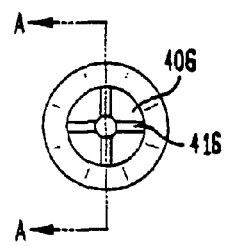
FIG. 11a is an end view of the extractor shown in FIG. 11.
Figure 11B:
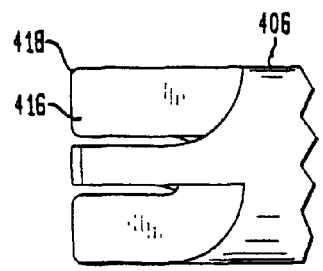
FIG. 11b is an enlarged detail of the drive and of the extractor shown in FIG. 11.

Referring to FIGS. 11 through 11b, there is shown a tool provided to remove the screw 105 after it has been fully inserted into bone and blocked from backing out by split-ring 104. Referring to FIG. 11 there is shown an extraction tool 400 having a handle 402 and a tubular drive shaft 404, including a drive tip 406. Handle 402 is also tubular having a cavity 408 open to an end 410 of handle 402. In the preferred embodiment, the cavity 408 is circular with a diameter of about 8 mm. Inner end 412 of cavity 408 is open to a cannulation 414 which extends the length of shaft 404 and through tip 406. In the preferred embodiment, this cannulation is circular with a diameter of about 2 mm. The function of cannulation 414 is described below.

Referring to FIG. 11b, there is shown an enlarged view of drive tip 406 of extraction tube 400 which, like driver head 306 previously described, includes a cruciform blade having cross members 416 similar to blades 308. However, the outer diameter of tip 406 is equal to the outer diameter of surface 156 on screw 105. Tip 406 includes an inwardly chamfered portion 418 which allows tip 406 to engage the inner diameter 145 of the split-ring and expand it sufficiently to allow the screw to be unthreaded or pulled back out through inner diameter 145 of screw 105 with extractor 400. Once the maximum diameter of upwardly facing surface 156 passes through the split-ring, it springs inwardly along surface 154 of screw 105.

Figure 12:
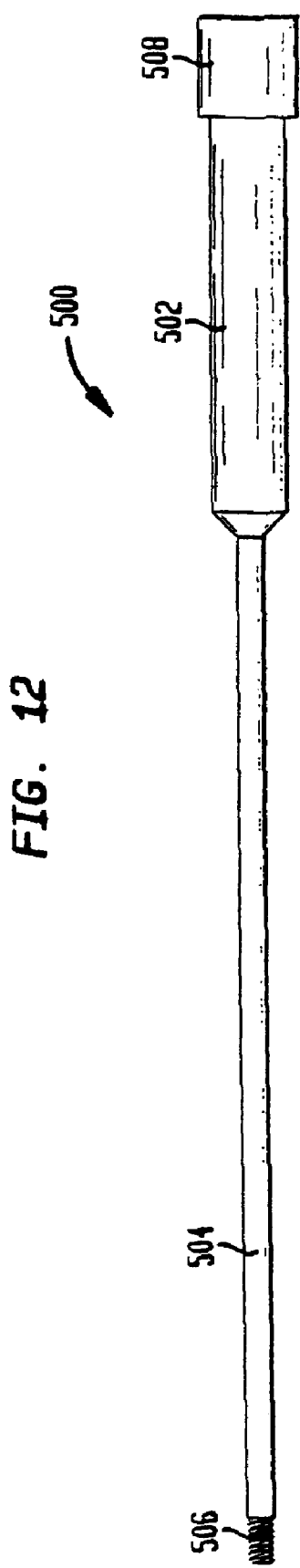
FIG. 12 is a plan view of a threaded extraction shaft designed to engage the screw and pull it axially out of the hole, should it be impossible to unscrew the threaded shank.

It has been found that in some instances, the bone deteriorates so that it is impossible to generate a screw removal force by the counter-rotation of screw 105 with extractor 400. In this instance, referring to FIG. 12, there is shown an extraction tool 500 designed to fit within the cavity 408 and cannulation 414 of extraction tool 400. Extraction tool 500 includes an upper portion 502, a shaft portion 504, a threaded tip 506 and an enlarged portion 508. The threaded tip includes threads matching threads 160 in screw 105. In the preferred embodiment, the thread is 1.6 mm in diameter. Thus, when the bone screw 105 cannot be removed merely by the counter-rotation of screw 105 with extraction tool 400, extraction shaft 504 is inserted through the cannulation 414 and out tip 406 thereof and into threaded engagement with threads 160 of bone screw 105. All the surgeon must then do is pull on portion 508 of the extraction tool 500 which pulls screw 105 out of the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant comprising:
a bone plate having a bone contacting surface and an opposite outwardly facing surface and first and second bone screw receiving openings each extending along a central axis between the outwardly facing surface and the bone contacting surface, a split-ring receiving recess open to the outwardly facing surface located intermediate the first and second bone screw receiving openings, the first and second bone screw receiving openings each having a slot spaced from the outwardly facing surface towards the bone contacting surface, a slot formed in a wall of the first and second bone screw receiving openings, each slot open to the split ring receiving recess; and
a resilient split-ring having a thickness less than a height of the slots in the first and second bone screw receiving openings along the bone screw receiving opening central axis, the split-ring having a contracted position wherein its dimension is less than a maximum dimension of the split-ring receiving recess and an expanded position wherein an outer circumference of the split-ring is larger than the maximum dimension of the recess and the split-ring extends through the slot in the wall of the first and second bone screw receiving openings towards the central axis and into the first and second bone screw receiving openings.

2. The implant as set forth in claim 1 wherein the split ring has a lug on each side of a split in the ring, each lug extending inwardly towards a center of the ring.

3. The implant as set forth in claim 1 wherein the recess comprises a counterbore bore extending to a depth intermediate the bone contacting and outer bone plate surfaces.

4. The implant as set forth in claim 3 wherein the counterbore has a planar base surface.

5. The implant as set forth in claim 4 wherein the planar base intersects a bottom surface of the slots in the wall of the first and second bone screw receiving openings.

6. The implant as set forth in claim 1 wherein the recess has a center offset from a line connecting center of the first and second bone screw receiving openings.

7. The implant as set forth in claim 6 wherein the center of the recess is equivalent from the centers of the first and second bone screw receiving holes.

8. The implant as set forth in claim 1 wherein the slots in the wall of the first and second bone screw opening are located closer to the bone plate outwardly facing surface than the bone contacting surface.

9. The implant as set forth in claim 8 wherein the wall of the first and second screw receiving bores includes a part-spherical portion.

10. The implant as set forth in claim 9 wherein the part-spherical wall portion intersects the outwardly facing bone surface of the bone plate.

11. An implant comprising:
a bone plate comprising a bone contacting surface and an outwardly facing surface spaced therefrom, at least first and second bone screw receiving holes with each hole having a center and a central axis through the centers; a recess open to the outwardly facing surface, the recess having a center spaced equidistant from the centers of the first and second bone screw receiving holes and a first and a second slot in a wall of the first and second bone screw receiving holes, the first and second slots open to the recess;
a split-ring having a thickness less than a height of the first and second slots measured along the central axis of the first and second bone screw receiving holes, the split-ring having a contracted diameter less than a diameter of the recess and a relaxed diameter greater than the diameter of the recess wherein an outer surface of the split-ring extends through the first and second slots in the wall of the first and second bone screw receiving holes towards the central axis and into the first and second bone screw receiving holes.

12. The implant as set forth in claim 11 wherein the split ring has a lug on each side of a split in the ring, each lug extending inwardly towards a center of the ring.

13. The implant as set forth in claim 11 wherein the recess comprises a counterbore bore extending to a depth intermediate the bone contacting and outer bone plate surfaces.

14. The implant as set forth in claim 13 wherein the counterbore has a planar base surface.

15. The implant as set forth in claim 14 wherein the planar base intersects a bottom surface of the slots in the wall of the first and second bone screw receiving openings.

16. The implant as set forth in claim 11 wherein the slots in the wall of the first and second bone screw opening are located closer to the bone plate outwardly facing surface than the bone contacting surface.

17. The implant as set forth in claim 16 wherein the wall of the first and second screw receiving bores includes a part-spherical portion.

18. The implant as set forth in claim 17 wherein the part-spherical wall portion intersects the outwardly facing bone surface of the bone plate.

* * * * *